United States Patent
Beckmann et al.

(10) Patent No.: US 6,890,674 B2
(45) Date of Patent: May 10, 2005

(54) METHODS AND APPARATUSES FOR MANAGING FLUIDS IN A FUEL CELL SYSTEM

(75) Inventors: Gerhard Beckmann, Altamont, NY (US); Robert S. Hirsch, Troy, NY (US)

(73) Assignee: MTI Microfuel Cells, Inc., Albany, NY (US)

(*) Notice: Subject to any disclaimer, the term of this patent is extended or adjusted under 35 U.S.C. 154(b) by 266 days.

(21) Appl. No.: 10/079,733

(22) Filed: Feb. 19, 2002

(65) Prior Publication Data

US 2003/0157385 A1 Aug. 21, 2003

(51) Int. Cl.[7] .......................... H01M 8/18; H01M 8/04; H01M 8/12
(52) U.S. Cl. .................. 429/24; 429/13; 429/20; 429/22; 429/26; 429/34
(58) Field of Search .................. 429/24, 13, 20, 429/22, 26, 34

(56) References Cited

U.S. PATENT DOCUMENTS

| | | | |
|---|---|---|---|
| 4,420,544 A | 12/1983 | Lawson et al. | 429/13 |
| 5,573,866 A | 11/1996 | Van Dine et al. | 429/13 |
| 5,599,638 A | 2/1997 | Surampudi et al. | 429/33 |
| 5,773,162 A | 6/1998 | Surampudi et al. | 429/39 |
| 5,795,496 A | 8/1998 | Yen et al. | 252/62.2 |
| 5,945,231 A | 8/1999 | Narayanan et al. | 429/30 |
| 5,992,008 A | 11/1999 | Kindler | 29/730 |
| 6,096,448 A * | 8/2000 | Wilkinson et al. | 429/13 |
| 6,289,888 B1 * | 9/2001 | Welles | 126/263.01 |
| 2002/0182474 A1 * | 12/2002 | Saito | 429/38 |

OTHER PUBLICATIONS

Abstract of JP402040865A, Feb. 9, 1990.*
Abstract of JP405290867, Nov. 5, 1993.*

* cited by examiner

*Primary Examiner*—Hoa Van Le
(74) *Attorney, Agent, or Firm*—Mintz, Levin, Cohn, Ferris, Glovsky and Popeo, P.C.

(57) ABSTRACT

A fuel cell system including an anode chamber having a fuel mixture comprising methanol and water, and a diffusion layer, a fuel source in fluid communication with the anode chamber via a conduit, a cathode chamber having a cathode and a diffusion layer, wherein the diffusion layer is in fluid communication with an oxidizer, and a proton conducting, electrical non-conducting membrane electrolyte separating the chambers and positioned substantially adjacent to said diffusion layers. The membrane includes a catalyst exposed to each of the chambers for initiating chemical reactions to produce electricity. The system also includes a first valve for automatically controlling a flow of fuel from the fuel supply cartridge, where the first valve includes a shape memory alloy.

39 Claims, 4 Drawing Sheets

METHODS AND APPARATUSES FOR MANAGING FLUIDS IN A FUEL CELL SYSTEM

BACKGROUND OF THE INVENTION

1. Field of the Invention

The invention relates generally to fuel cell systems, and more particularly, the invention relates to methods and apparatuses for controlling fuel flow and sensing fuel concentration in a fuel cell system.

2. Background of the Invention

Fuel cells are devices in which an electrochemical reaction is used to generate electricity. A variety of materials may be suitable for use as a fuel depending upon the materials chosen for the components of the cell and the intended application for which the fuel cell will provide electric power.

Fuel cell systems may be divided into "reformer based" systems (which make up the majority of currently available fuel cells), in which fuel is processed to improve fuel cell system performance before it is introduced into the fuel cell, and "direct oxidation" systems in which the fuel is fed directly into the fuel cell without internal processing.

Because of their ability to provide sustained electrical energy, fuel cells have increasingly been considered as a power source for smaller devices including consumer electronics such as portable computers and mobile phones. Accordingly, designs for both reformer based and direct oxidation fuel cells have been investigated for use in portable electronic devices. Reformer based systems are not generally considered a viable power source for small devices due to size and technical complexity of present fuel reformers.

Thus, significant research has focused on designing direct oxidation fuel cell systems for small applications, and in particular, direct systems using carbonaceous fuels including but not limited to methanol ethanol and aqueous solutions thereof. One example of a direct oxidation fuel cell system is a direct methanol fuel cell system. A direct methanol fuel cell power system is advantageous for providing power for smaller applications since methanol has a high energy content, thus providing a compact means of storing energy, can be stored and handled with relative ease, and because the reactions necessary to generate electricity occur under ambient conditions.

DMFC power systems are also particularly advantageous since they are environmentally friendly. The chemical reaction in a DMFC power system yields only carbon dioxide and water as by products (in addition to the electricity produced). Moreover, a constant supply of methanol and oxygen (preferably from ambient air) can continuously generate electrical energy to maintain a continuous, specific power output. Thus, mobile phones, portable computers, and other portable electronic devices can be powered for extended periods of time while substantially reducing or eliminating at least some of the environmental hazards and costs associated with recycling and disposal of alkaline, Ni—MH and Li-Ion batteries.

The electrochemical reaction in a DMFC power system is a conversion of methanol and water to $CO_2$ and water. More specifically, in a DMFC, methanol, preferably in an aqueous solution, is introduced to the anode face of a protonically-conductive, electronically non-conductive membrane in the presence of a catalyst. When the fuel contacts the catalyst, hydrogen atoms from the fuel are separated from the other components of the fuel molecule. Upon closing of a circuit connecting a flow field plate of the anode chamber to a flow field plate of the cathode chamber through an external electrical load, the protons and electrons from the hydrogen atoms are separated, resulting in the protons passing through the membrane electrolyte and the electrons traveling through an external load. The protons and electrons then combine in the cathode chamber with oxygen producing water. Within the anode chamber, the carbon component of the fuel is converted by combination with water into $CO_2$, generating additional protons and electrons.

The specific electrochemical processes in a DMFC are:

Anode Reaction: $CH_3OH + H_2O = CO_2 + 6H^+ + 6e$

Cathode Reaction: $3/2O_2 + 6H^+ + 6e = 2H_2O$

Net Reaction: $CH_3OH + 3/2O_2 = CO_2 + H_2O$

The methanol in a DMFC is preferably used in an aqueous solution to reduce the effect of "methanol crossover". Methanol crossover is a phenomenon whereby methanol molecules pass from the anode side of the membrane electrolyte, through the membrane electrolyte, to the cathode side without generating electricity. Heat is also generated when the "crossed over" methanol is oxidized in the cathode chamber. Methanol crossover occurs because present membrane electrolytes are permeable (to some degree) to methanol and water. One method of reducing methanol crossover is to introduce the methanol in an aqueous solution, thus providing the fuel cell with little more methanol than is required, minimizing crossover without depriving the fuel cell of the necessary fuel.

One of the problems with using DMFC power systems in portable power applications is the lack of a low-cost, effective method for controlling the concentration of methanol fuel in the fuel mixture. Specifically, a problem exists in keeping the proper ratio of fuel to water delivered to the anode chamber in DMFC power systems. For example, if the methanol concentration on the anode face of the membrane electrolyte is too high, then methanol crossover is likely to occur. Similarly, when a fuel cell is too hot, it may encourage excess methanol crossover. Methanol crossover not only wastes fuel, and increases the heat of the fuel cell, but can contribute to cathode flooding, which compromises the performance of the fuel cell.

Because saturation of the cathode prevents the energy producing reactions from proceeding, excess water on the cathode side of the membrane can lead to an increase in methanol concentration at the anode. The increased concentration of methanol may then lead to additional methanol crossover resulting in decreased efficiency, a waste of methanol, and the generation of unwanted heat.

According, the suitability of DMFC power systems for powering portable devices and consumer electronics is dependent upon the development of systems and methods for controlling the amount of fuel concentration in the fuel mixture of a direct methanol fuel cell.

Moreover, it is desirable to utilize physical properties of materials and mechanisms to control the behavior of a fuel cell (i.e., passive components/systems), to reduce product costs and system complexity.

SUMMARY OF THE INVENTION

Accordingly, the present invention provides devices and methods for managing fuel concentration in a fuel mixture for a fuel cell. More particularly, the present invention provides simple devices and methods for controlling fuel concentration which rely on the intrinsic properties of the materials used to fabricate the fuel cell and fuel cell system. The devices and methods are according to the present invention are particularly well suited for use with a direct oxidation fuel cell system.

It is desired to allow physical properties of materials and mechanisms to control the behavior of a fuel cell and/or other associated devices incorporating fuel flow control while generating heat. By using such passive systems, costs can be reduced as well as system complexity. In addition, because such a system will have fewer valves and controls, this system will be easier to manufacture on a commercial scale, and will be more reliable than other more complex systems.

Accordingly, the below recited aspects of the present invention are directed to direct oxidation fuel cell systems, and more preferably to direct methanol fuel cell power systems.

In one aspect of the present invention, a fuel cell includes a housing having an anode chamber in communication with a fuel source via a conduit, a cathode chamber in fluid communication with an oxidizing agent, a proton conducting membrane electrolyte separating the chambers, and a heat-actuated valve proximate the conduit for controlling a flow of fuel from the fuel source to the anode chamber.

In another aspect of the present invention, a method for controlling flow in a fuel cell includes connecting said fuel cell to an electrical load, producing electrical energy, generating heat in response to the production of electricity by the fuel cell, and automatically actuating a heat-sensitive valve for controlling fuel flow into said fuel cell upon the occurrence of a predetermined temperature of the fuel cell as a result of the heat.

In another aspect of the present invention, a fuel cell includes a housing having an anode chamber with a fuel mixture, with the anode chamber in communication with a fuel source, a cathode chamber in fluid communication with an oxidizing agent, a proton conducting membrane electrolyte separating the chambers, and a fuel concentration-actuated valve for automatically controlling a flow of fuel from the fuel source to the anode chamber.

In yet another aspect of the present invention, a method for controlling flow in a fuel cell includes connecting the fuel cell to an electrical load, producing electrical energy, providing fuel to a fuel mixture of the fuel cell in response to producing the electricity, and expanding a first material in response to a fuel concentration of the fuel mixture. The expansion of the first material controls the flow of fuel into the fuel mixture.

In another aspect of the present invention, a sensor for determining a concentration of fuel in a fuel mixture for a fuel cell includes a conductor that is either in intimate contact with, applied to, or mechanically fastened to a first material. The first material includes an intrinsic property which causes the first material to expand upon exposure to methanol.

In still yet another aspect of the present invention, a method for determining a concentration of fuel in a fuel cell includes providing a first material capable of expanding in response to a concentration of fuel in a fuel cell, where within the first material a conductor is positioned which includes a plurality of individual particle portions. Upon a low concentration of fuel, a substantial portion of adjacent particles contact one-another. The method also includes passing an electrical current through the conductor, and measuring the electrical resistance of the conductor. As the fuel concentration is changes, resistance of the conductor changes in proportion (stretching, e.g., stretching the particles apart) to the fuel concentration. Accordingly, the fuel concentration can be determined based upon the change in resistance of the conductor.

In another aspect of the present invention, a direct methanol fuel cell system includes an anode chamber having a fuel mixture comprising methanol and water, and a diffusion layer, a fuel supply cartridge in fluid communication with the anode chamber via a conduit, and a cathode chamber having a cathode and a diffusion layer. The diffusion layer is in fluid communication with an oxidizer. The system also includes a proton conducting, electronically non-conducting membrane electrolyte separating the chambers and positioned substantially adjacent to, and in intimate contact with each of the diffusion layers, which membrane includes a catalyst exposed to of the diffusion layers. The system further includes a first valve for automatically controlling a flow of fuel from the fuel supply cartridge to the fuel mixture, where the valve includes a shape memory alloy.

In another aspect of the present invention, a switch for a fuel cell is provided. The fuel cell includes a housing having an anode chamber in communication with a fuel source, a cathode chamber in fluid communication with an oxidizing agent, and a proton conducting membrane electrolyte separating the chambers. The switch includes a heat-actuated shape memory alloy where below a predetermined temperature, the switch is in a first position and upon the fuel cell reaching the predetermined temperature, the switch is switched to a second position.

In yet another aspect of the present invention, a switch for a fuel cell (as described above) is provided. The switch includes a first material having expansion properties upon exposure to water, where the switch is in a first position prior to exposure to water and in a second position after the first material is exposed to water.

BRIEF DESCRIPTIONS OF THE DRAWINGS

For a better understanding of the invention, reference is made to the drawings which are incorporated herein by reference and in which.

DETAILED DESCRIPTION OF THE PREFERRED EMBODIMENTS

Figure 1:
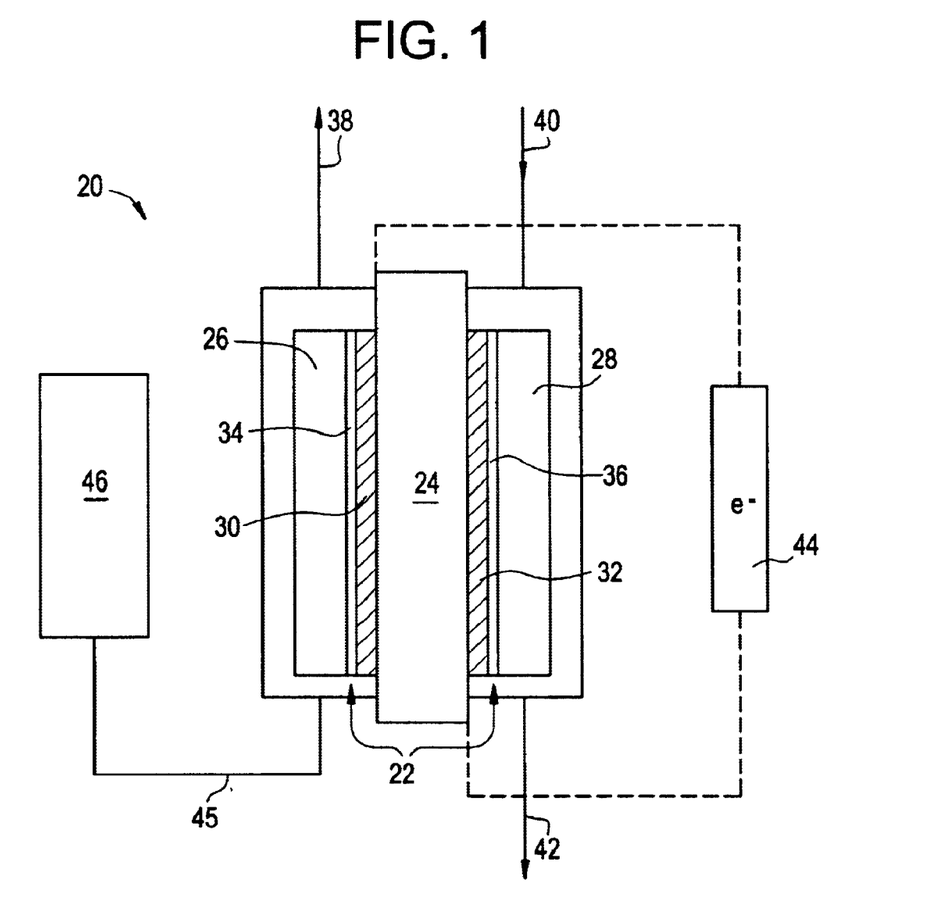
FIG. 1 illustrates a fuel cell system for which the features of the present invention may be aptly used.

As shown in FIG. 1, a schematic diagram of one embodiment of a direct oxidation fuel cell system 20 includes a membrane electrolyte assembly 22 having a proton-conducting, electronically non-conductive membrane electrolyte 24 disposed between an anode chamber 26 and a cathode chamber 28. The exact shape of the anode chamber and cathode chamber may be defined by a "flow field channel" which may, but need not be, be integrated into a flow field plate (not shown), which aids in distributing the fuel and the oxidizing agent to the membrane electrolyte. In this diagram, each surface of the membrane electrolyte 24 is coated with electrocatalysts which serve as anode reactive sites 30 on the anode chamber side of the membrane and cathode reactive sites 32 on the cathode chamber side of the membrane. Fuel is provided to the anode chamber 26 from a fuel source 46 (e.g., a fuel cartridge) via a conduit 45. The anode and cathode reactive sites facilitate the electrochemical reactions of the DMFC.

It is worth noting that the electrocatalysts may be provided in other areas within the anode and cathode chambers, and thus, the invention is not limited to fuel cells where the catalysts are provided on the membrane electrolyte. Rather the invention is applicable to any fuel cell system where it is desirable to control the flow of fluids within the fuel cell system.

Diffusion layers 34 and 36, may be included and positioned on either side of the membrane. These layers provide a uniform effective supply of methanol solution (diffusion layer 34) to the anode reactive sites and a uniform effective supply of oxidizing agent (diffusion layer 36) to the cathode reactive sites. Diffusion layers 34 and 36 on each of the anode and cathode sides of the membrane electrolyte also assist in providing optimal humidification of the membrane electrolyte by assisting in the distribution and removal of water to and from the membrane electrolyte at rates that maintain a proper water balance in the DMFC power system. Moreover, each layer may be used with a flow field (not shown), to further aid in distributing fuel and oxidizer to the respective reactive sites.

As previously stated, the anode chamber of the fuel cell for which features of the present invention may be used also includes the flow field plate (not shown) which also functions as a conductor (i.e., acts as the electrical anode), and an exhaust vent 38 which allows carbon dioxide created during oxidation of the fuel to pass out of the anode chamber. Similarly, the cathode chamber may include a flow field plate (not shown) which guides oxidizing agent in the chamber and also functions as a conductor (i.e., acts as the electrical cathode), an inlet 40 and an exhaust outlet 42 which allows air to flow through the cathode chamber so that an adequate supply of oxygen is insured for the reaction. One skilled in the art will appreciate that air may flow from inlet 40 to outlet 42 and in the opposite direction, when the system is exposed to an ambient air pressure.

In a DMFC power system, an aqueous methanol solution, preferably a solution greater than 0% to about 100% methanol stoichiometrically, and more preferably between greater than 0% to about 50% methanol stoichiometrically is introduced as the carbonaceous fuel reactant. The methanol solution circulates past the anode reactive sites 30. Upon the application of an electrical load between the flow field plates of the anode and the cathode chambers, the methanol solution disassociates, producing hydrogen protons and electrons, and generating carbon dioxide as a first by-product of fuel oxidation. Hydrogen protons migrate through the membrane electrolyte to the cathode chamber while electrons pass through the external load. The protons and electrons then combine with oxygen in the cathode chamber to form water, the second by-product of the reaction. The electrons are retrieved by the flow field plate of the anode chamber and carried through an external electrical load 44 to the flow field plate of the cathode chamber.

First Embodiment

In a first embodiment of the present invention, flows of fuel, gases, liquids and effluents is controlled by a heat-sensitive switch/valve. A particular aspect of the present invention is directed to controlling the flow of fuel from the fuel source to a mixing chamber, an anode chamber or to a pump. With this embodiment, as the operating temperature of the fuel cell increases, the flow of fuel is either increasingly restricted by the switch/valve or quickly restricted. Ultimately, upon the fuel cell reaching a predetermined operating temperature, the flow of fuel is completely shut-off by the novel switch/valve.

The first embodiment is realized via use of bi-metals and shape memory alloys used as springs. Bi-metal springs are springs where two metals are bonded together which have different thermal strain rates. As the by-metal spring is heated, the strip bends allowing it to perform work. Shape memory alloys, on the other hand, undergo a phase transformation in their crystal structure when cooled from a stiffer, high temperature form (Austenite) to a more malleable, low temperature form (Martensite), giving the alloys shape memory and superelasticity.

When a shape memory alloy is in its martensitic form, it is easily deformed to a new shape. However, when the alloy is heated through its transformation temperatures, it reverts to austenite and recovers its previous shape with great force. This process is known as shape memory.

The temperature at which the shape memory alloy returns to its high temperature form when heated can be adjusted by slight changes in alloy composition and through heat treatment. In NiTi (nickel-titanium, e.g., Nitanol) alloys, for example, the temperature can be changed from above +100 deg. C. to below −100 deg. C. The shape recovery process occurs over a range of just a few degrees and the start or finish of the transformation can be controlled to within a degree or two if necessary.

Figure 2:
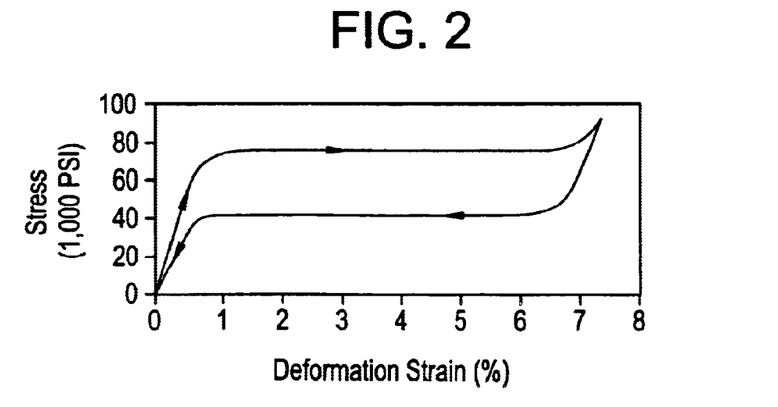
FIG. 2 is graph illustrating the loading and unloading behavior of superelastic NiTi alloy.

Supereleastic behavior can be accomplished if the alloy is deformed at a temperature which is slightly above their transformation temperatures. This effect (shown in graphical form in FIG. 2) is caused by the stress-induced formation of some martensite above its normal temperature. Because it has been formed above its normal temperature, the martinsite reverts immediately to undeformed austenite as soon as the stress is removed. This process provides a very springy, rubber-like elasticity in these alloys, and can create sufficient force to open or close a valve.

Figure 3:
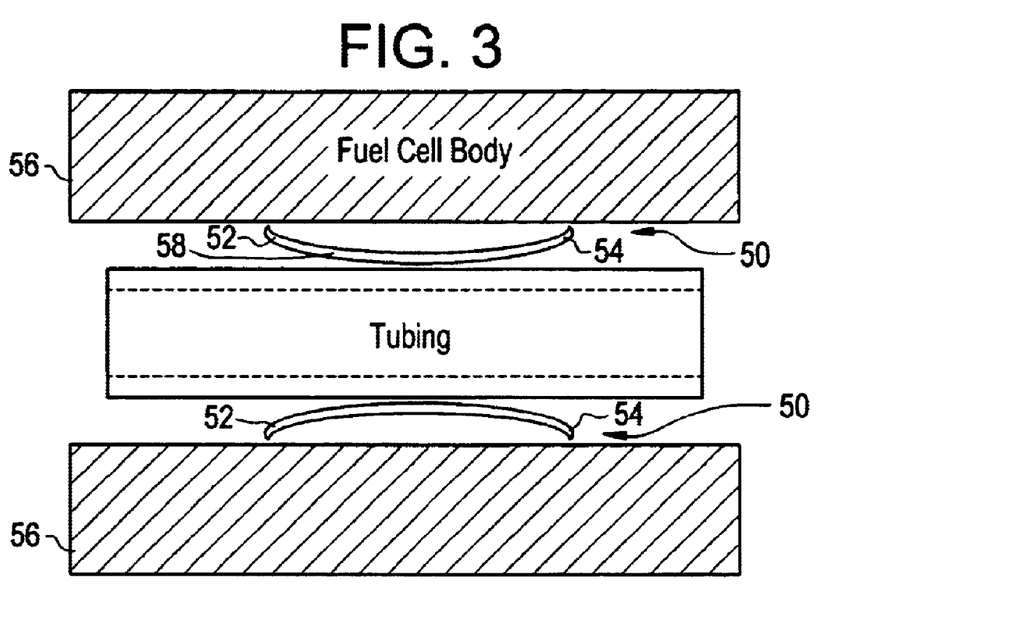
FIG. 3 illustrates a cross-section of a fuel delivery conduit for a fuel cell system, showing an open conduit and open, heat-actuated valves.
Figure 4:
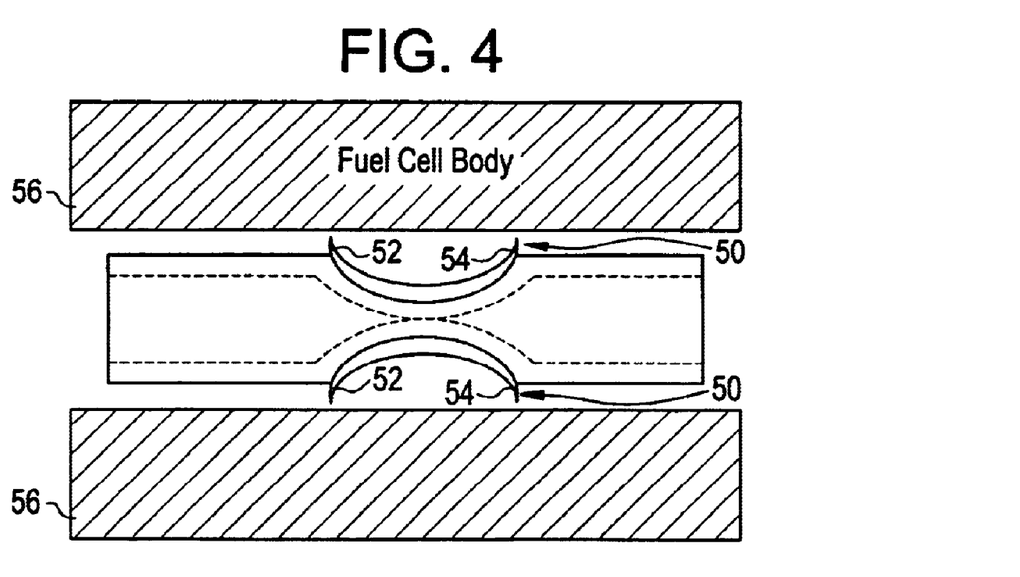
FIG. 4 illustrates a cross-section of a fuel delivery conduit for a fuel cell system, showing a closed conduit and closed, heat actuated valves.

Accordingly, the first embodiment of the present invention uses the above materials to create a heat sensitive switch/valve for controlling the flow of fuel; preferably, such materials are shape memory alloys, with a nickel titanium alloy being most preferable. As shown in FIGS. 3 and 4, pieces of shape memory alloy (SMA) are placed adjacent a flexible fuel flow tube which is positioned proximate a portion of the fuel cell body which adequately reflects the temperature of the fuel cell (shape memory alloy springs are illustrated, but bi-metal springs include a similar arrangement).

When the fuel cell is connected to an electrical load, and electricity is produced, the fuel cell begins to heat up as a result of the chemical reaction of methanol with the catalysts contained within the fuel cell. As such, the threshold temperature can be calibrated such that the SMA is activated if a certain temperature is exceeded, thus adjusting the flow of reactants to prevent the fuel cell system from overheating.

When the fuel cell becomes too hot, may indicate a high fuel crossover rate, or excessive demand on the fuel cell Each of which may excessively stress the system, which may result in an increased in liquid buildup on the cathode, or CO2 buildup on the anode, among other problems, leading ultimately to a slowing reaction and lowered electricity production. Where multiple inventive valves are implemented within a single system, they may be configured to transform at different temperatures, thus providing different responses under a variety of conditions. The SMA spring is placed at desired locations adjacent the flexible fuel flow tube and proximate a portion of the fuel cell having a temperature corresponding to the operational temperature of the fuel cell. When the temperature of the fuel cell portion reaches a predetermined temperature, the SMA spring reverts to its austenite shape, where the center of the spring bends inward toward the center of the flexible flow tube, thereby immediately closing the flexible tube in on itself and cutting off the fuel supply. Of course, the SMA spring is preferably shaped and designed such that the interference of the fuel flow occurs only when a predetermined first temperature of the fuel cell is reached.

Depending upon the design of the fuel cell, the actuation of the SMA spring can be custom tailored for temperatures as well as to the effect on the supply of fuel. Specifically, the spring may be designed such that upon activation, fuel is slowed to a predetermined point, or is completely shut off.

Accordingly, as shown in FIGS. 3 and 4, SMA springs 50 include a first end 52 positioned against a conduit wall 56, and a second end 54 positioned against conduit wall 56. The SMA spring may include a slight visible curve 58, alluding to the direction upon which the SMA spring will bend, however, this curve may be so slight that it is not wholly visible to the naked eye.

Although the present invention is shown and described using two SMA springs, a single SMA spring may be easily designed to perform the intended valve/switch function. The SMA springs can be shaped and programmed to pinch a flexible tube at a certain cell temperature, thereby restricting the liquid flow totally or in part. Moreover, the spring shape illustrated need not be in the shape of a leaf spring. The SMA spring may be shaped as a coil spring which crimps the flexible tube on its own without pushing against an object.

Alternatively, a spring may allow the introduction of water or a more dilute mixture if a certain temperature is reached, by placing a spring that, in its Martensite configuration prevents the flow of a fluid, but which when its austenite state is attained, it allows the flow of a desired fluid.

Figure 5:
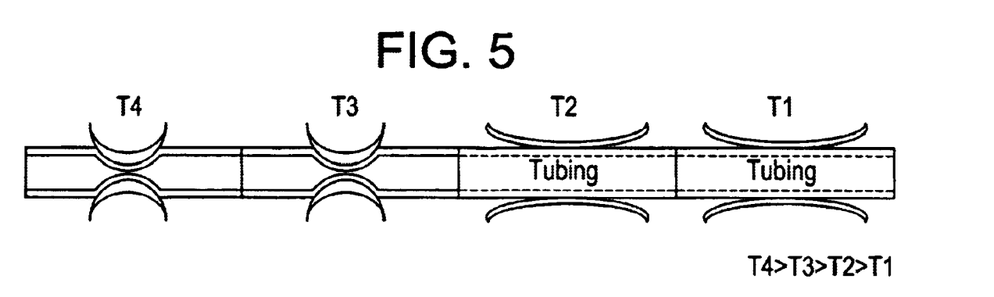
FIG. 5 illustrates a plurality of a heat-actuated valves according to the present invention.

As stated earlier, bi-metal springs (BM) may also be used to implement this characteristic. BM springs have the effect of increasingly interfering with the affected flow since the characteristic of their bending is that they continually bend upon increasing temperature. In contrast, SMA springs remain in one shape, then revert back to an austenite shape upon a predetermined temperature. This idea of the restriction of fuel flow with a BM spring valve based on temperature can be best understood with reference to FIG. 5. As shown, temperatures T4 is greater than temperature T3, which is greater than temperature T2, which is greater than temperature T1. These temperatures represent, for example, initial startup temperature (T1), a temperature a first predetermined time after startup in which fuel flow is starting to be restricted (T2), a temperature after a second predetermined time after startup in which fuel flow is increasingly restricted (T3), and a temperature after the fuel cell has reaches the threshold temperature in which fuel is effectively shut-off (T4).

Accordingly, for both SMA springs and BM springs, when the operating temperature of the fuel cell decreases because of fuel restriction by the spring valve or via switching off the electrical load, either the spring completely retracts (SMA springs), or the spring retracts to a position corresponding to the temperature (BM) spring.

Second Embodiment

The second embodiment of the present invention is directed to the use of a material which expands upon exposure of methanol. More particularly, the second embodiment is directed to a material whose expansion is directly related to a concentration of methanol fuel in a fuel solution. Such a feature may be used as a switch, valve or sensor in a fuel cell.

Figure 6:
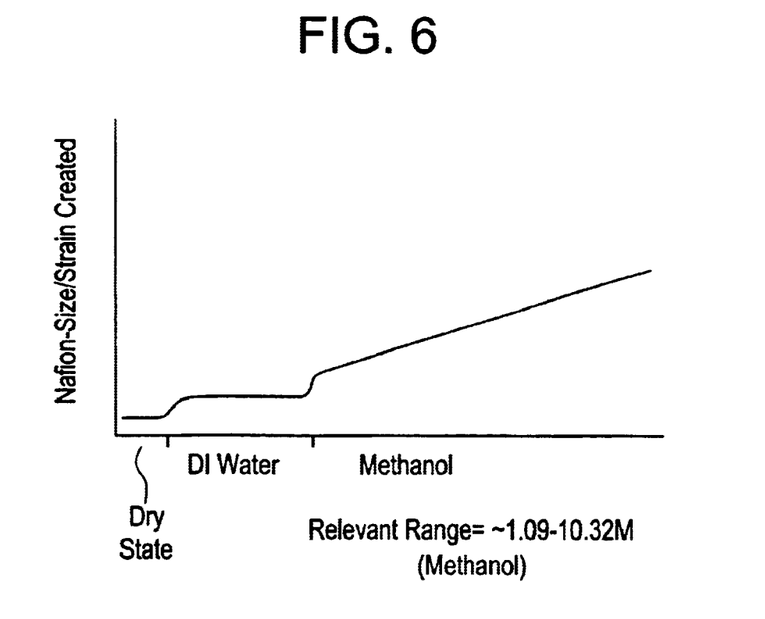
FIG. 6 is a graph illustrating the expansion/strain of Nafion in response to methanol concentration.

A material having these qualities is Nafion® 117, manufactured by E.I. du Pont de Nemours and Company of Wilmington, Del., As shown in FIG. 6, which is a graph of size/strain created versus percentage of methanol in solution, Nafion includes a first size in a dry state, a somewhat expanded form when exposed to water, and then a proportional size depending upon a percentage of methanol in solution. The amount which Nafion 117 expands is predictable and essentially linear over the relevant methanol concentrations. As such, the expansion of Nafion can be used to actuate a switch or a valve to control a flow in a fuel cell.

Figure 7A:
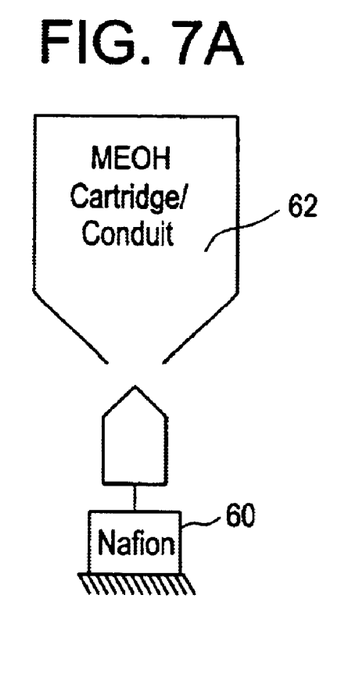
FIG. 7A illustrates an overview of a Nafion fuel flow valve for a fuel cell in an open position.
Figure 7B:
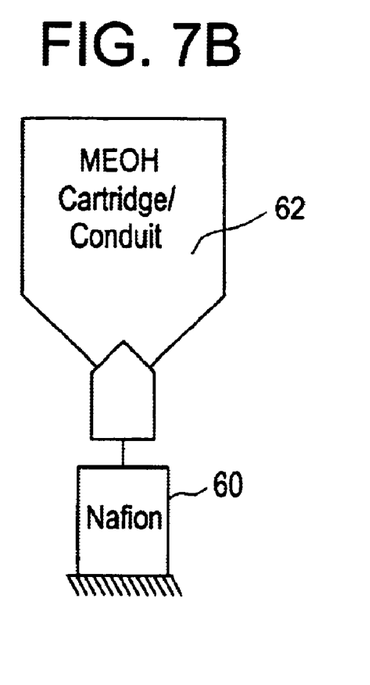
FIG. 7B illustrates an overview of a Nafion fuel flow valve for a fuel cell in a closed position.

For example, as shown in FIGS. 7A and 7B, a piece of Nafion like material 60 may be used as a valve actuator in a fuel cartridge 62 or conduit. As shown, upon a low concentration of methanol, the Nafion remains at a first size in FIG. 7A where fuel is allowed to freely flow from the cartridge to be ultimately used in the anode chamber. However, the Nafion member begins to expand as the level of methanol increases. Once the concentration reaches a predetermined percentage, the Nafion has expanded such that it now closes a valve supplying fuel to the reaction. Those skilled in the art will recognize that there are numerous ways in which a switch could be mechanically actuated.

Figure 8:
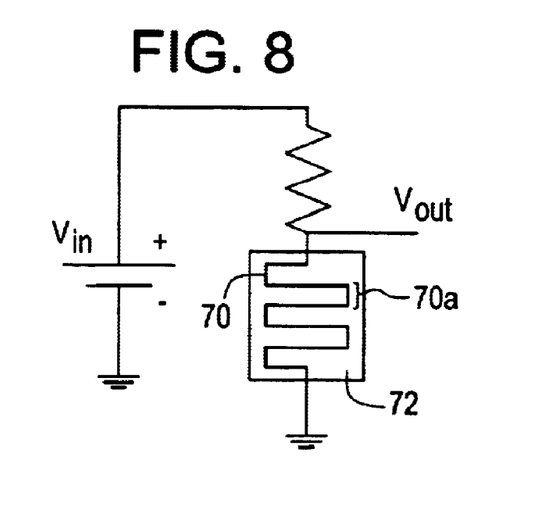
FIG. 8 illustrates an electrical fuel concentration sensor using a Nafion like material.

As used as a sensor, Nafion can easily communicate a concentration level of methanol. Accordingly, as shown in FIG. 8, a conductor 70 (having, for example, particle portions 70a) is applied to or mechanically fastened to a piece of Nafion or other similar material 72. In this embodiment, the conductor is laid on such material in a serpentine pattern (for example) and has a current passing through it. The conductor, also, has a known resistance value under certain states of strain and a known set resistance value, where the total resistance value of the conductor as a whole changes depending upon the degree to which the conducting particles are in contact with each other. Thus, if the conductor is in a relaxed, rather than a strained state, the conductive particles are largely in contact with one another, and the total resistance value of the conductor is a first value.

Upon exposure of the Nafion conductor methanol concentration sensor, the Nafion expands. As the Nafion expands, the contact between the conductive particles of the conductor is diminished, and thus the resistance of the conductor increases proportionally. Thus, the inventors have found that the change in resistance of the conductor within the Nafion based upon the present invention is directly proportional to the concentration of methanol in a methanol solution.

Such a system can be easily fabricated and integrated into a fuel cell to directly monitor fuel concentration. With regard to monitoring the resistance of the conductor, a simple Wheatstone bridge circuit may be used to determine the actual resistance. Thus, the resistance values are compared to known values associated with particular fuel concentrations.

Figure 9:
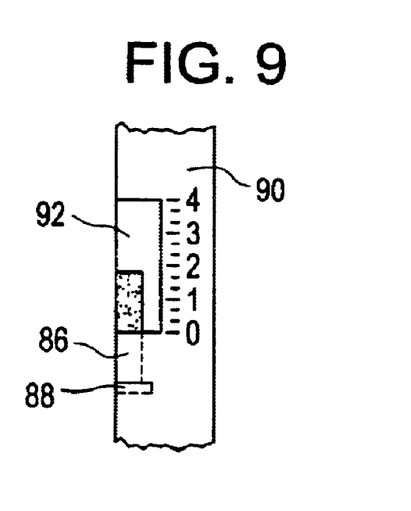
FIG. 9 illustrates a visual fuel concentration sensor using a Nafion like material.

Other materials with identified properties may also be used as a visual sensor as shown in FIG. 9. There, Nafion like material is displayed in a window element to visually gauge fuel concentration to a written scale located adjacent the window. Specifically, a conduit 80 having the fuel mixture of the anode (or direct access thereto) includes window 82, having a written legend 84 comprising fuel concentration values (e.g., 0–4%). A Nafion like material 86, having one end fastened to a anchor 88 of the conduit is placed adjacent the window. Thus, with increasing fuel concentration, the Nafion like material expands. The top end is then compared to the visible scale to determine the fuel concentration.

The embodiments described above may be used not only as a valve, but also as a sensor and a switch for any associated switching application in a fuel cell. Such applications include valves for fuel flow, air flow, flushing effluents and the like.

Having described the invention with reference to the presently preferred embodiments, it should be understood that numerous changes in creating and operating such systems and methods may be introduced without departing from the true spirit of the invention as defined in the appended claims.

What is claimed is:

1. A fuel concentration-actuated valve for controlling a fluid flow in a fuel cell comprising a first material which expands in direct relation to fuel concentration.

2. The fuel concentration-actuated value according to claim 1, wherein the first material comprises a perfluorosulfonic acid polymer.

3. A fuel cell comprising:
a housing including an anode chamber, a cathode chamber, a protonically conductive, substantially electronically non-conductive membrane electrolyte separating said chambers; and
a thermally sensitive actuator for controlling a flow of a fluid to/from the fuel cell.

4. The fuel cell according to claim 3, wherein said flow comprises a flow fuel or a flow of water.

5. The fuel cell according to claim 3, wherein the anode chamber is in fluid communication with a fuel source and wherein said flow comprises a flow of fuel or a fuel mixture to the anode chamber.

6. The fuel cell according to claim 5, wherein said fuel source communicates with said anode chamber via a conduit.

7. The fuel cell according to claim 6, wherein said thermally-sensitive actuator is proximate said conduit.

8. The fuel cell according to claim 6, wherein a temperature of said conduit reflects an operational temperature of said fuel cell.

9. The fuel cell according to claim 3, wherein said thermally-sensitive actuator comprises a bi-metal material and/or a shape-memory alloy.

10. The fuel cell according to claim 9, wherein said shape memory alloy comprises nickel and/or titanium.

11. The fuel cell according to claim 6, wherein said conduit includes a deformable material.

12. The fuel cell according to claim 5, wherein said fuel source is selected from the group consisting of: a fuel cartridge, a pump, and a mixing chamber.

13. The fuel cell according to claim 11, wherein said actuator is positioned adjacent said deformable material.

14. A fuel cell comprising:
a housing including an anode chamber having a fuel mixture, said anode chamber in communication with a flow for adjusting the concentration of said fuel mixture, a cathode chamber, a protonically conductive, substantially electronically non-conductive membrane electrolyte separating said chambers; and
a fuel concentration-actuated valve for controlling said fluid flow.

15. The fuel cell according to claim 14, wherein said flow comprises a fuel flow or a water flow.

16. The fuel cell system according to claim 14, wherein said fuel mixture includes methanol.

17. The fuel cell according to claim 14, wherein said fuel concentration-actuated valve comprises a first material which expands in direct relation to fuel concentration.

18. The fuel cell according to claim 17, wherein said first material comprises a perfluorosulfonic acid polymer.

19. A sensor for determining a concentration of fuel in a fuel mixture for a fuel cell comprising a conductor disposed on or within a first material, wherein said first material expands in proportion to the concentration of fuel based on exposure to a fluid.

20. A sensor for determining the presence of a fuel in a fuel cell comprising a conductor disposed on or within a first material, wherein said first material expands in proportion to the concentration of fuel based on exposure to a fluid.

21. The sensor according to claim 19 or 20, wherein said fluid is water, methanol or a methanol/water mixture.

22. A direct methanol fuel cell system comprising:
an anode chamber having an anode and a diffusion layer, wherein a fuel is introduced to the anode chamber via the diffusion layer;
a fuel source in fluid communication with said anode chamber;
a cathode chamber having a cathode and a diffusion layer, wherein said diffusion layer is in fluid communication with an oxidizer; and
a protonically conductive, substantially, electronically non-conductive membrane electrolyte separating said chambers and positioned substantially adjacent to said diffusion layers; and
a first valve for controlling a flow of a fluid in response to an operating parameter of the fuel cell system.

23. The system according to claim 22, where said valve comprises a thermally-sensitive actuator.

24. The system according to claim 23, wherein said thermally-sensitive actuator comprises a shape memory material or alloy.

25. The system according to claim 22, wherein said operating parameter comprises temperature and/or fuel concentration.

26. The system according to claim 22, wherein said valve comprises a first material capable of expansion proportional to a change in fuel concentration.

27. The system according to claim 26, wherein the first material comprises a perfluorosulfonic acid polymer.

28. A switch for a fuel cell, said fuel cell comprising a housing including an anode chamber, a cathode chamber, a protonically conductive, substantially electronically non-conductive, membrane electrolyte separating said chambers, said switch comprising:
a thermally-sensitive material wherein below a predetermined temperature, said switch is in a first position, and upon said fuel cell reaching said predetermined temperature said switch is switched to a second position.

29. The switch according to claim 28, wherein said thermally sensitive material comprises a shape memory alloy.

30. The switch according to claim 29, wherein said thermally-actuated shape memory alloy comprises nickel and/or titanium.

31. The switch according to claim 28, wherein said switch is disposed proximate to a portion of said fuel cell which reflects a current operational temperature of said fuel cell.

32. The switch according to claim 28, wherein a positioning of said switch between said first position and said second position is variable depending upon an operating temperature of said fuel cell.

33. A switch for a fuel cell, said fuel cell comprising a housing including an anode chamber, a cathode chamber, a protonically conductive, substantially electronically non-conductive, membrane electrolyte separating said chambers, said switch comprising:

a first material having expansion properties upon exposure to a fluid, wherein said switch is in a first position prior to exposure to said fluid and said switch is in a second position after said first material is exposed to said fluid.

34. The switch according to claim 33, wherein a positioning of said switch between said first position and said second position is variable in a non-linear aspect in relation to an amount of said fluid said first material is exposed to.

35. The switch according to claim 33, wherein said switch is placed in a third position upon exposure of said first material to a concentration of a second fluid.

36. The switch according to claim 33, wherein the fluid comprises water or methanol.

37. The switch according to claim 33, wherein an actual position of said third position is directly dependent upon said concentration of methanol.

38. A thermally sensitive actuator for controlling a flow of a fluid to/from the fuel cell comprising a bi-metal material and/or a shape-memory alloy.

39. The actuator according to claim 38, wherein said shape memory alloy comprises nickel and/or titanium.

* * * * *